United States Patent [19]
Vonderharr et al.

[11] Patent Number: 6,099,566
[45] Date of Patent: Aug. 8, 2000

[54] PROSTHETIC IMPLANT VALVE COVER

[75] Inventors: Kevin Vonderharr, Andover; Jason T. Papenfuss, Chanhassen; Stephen M. Trinter, Eden Prairie; Paul Turley, St. Louis Park, all of Minn.

[73] Assignee: PMT Corporation, Chanhassen, Minn.

[21] Appl. No.: 09/146,905

[22] Filed: Sep. 4, 1998

[51] Int. Cl.[7] .................................................. A61F 2/12
[52] U.S. Cl. .................................................................. 623/8
[58] Field of Search .......................... 623/8, 7; 138/96 R, 138/89; 604/256; 446/222; 137/233, 234; 251/319

[56] References Cited

U.S. PATENT DOCUMENTS

| | | | |
|---|---|---|---|
| 4,253,201 | 3/1981 | Ross et al. | 623/8 |
| 4,671,255 | 6/1987 | Dubrul et al. | 623/7 |
| 5,022,942 | 6/1991 | Yan et al. | 623/8 X |
| 5,108,430 | 4/1992 | Ravo | 623/12 |
| 5,119,842 | 6/1992 | Jaw | 446/222 X |
| 5,456,716 | 10/1995 | Iversen et al. | 623/8 |
| 5,611,792 | 3/1997 | Gustafsson | 623/8 X |
| 5,662,708 | 9/1997 | Hayes et al. | 623/8 |

*Primary Examiner*—Michael J. Milano
*Assistant Examiner*—Brian E. Pellegrino
*Attorney, Agent, or Firm*—Anthony G. Eggink

[57] ABSTRACT

A valve cover for a prosthetic implant. The valve cover is adhered to the prosthetic implant and covers the fill valve. The valve cover has a flexible body having an upper portion, a central portion and a lower portion. A plug extends from the bottom surface of the central portion of the valve cover body. A continuous textured peripheral area is disposed on the bottom surface of the flexible body and which extends through the upper portion and to the lower portion through an axis intersecting the valve entrance. The continuous peripheral area is adhered to the prosthetic implant body whereby the plug is aligned with the fill valve entrance. Lifting of the lower portion of the valve cover provides access to the fill valve of the prosthetic implant.

20 Claims, 3 Drawing Sheets

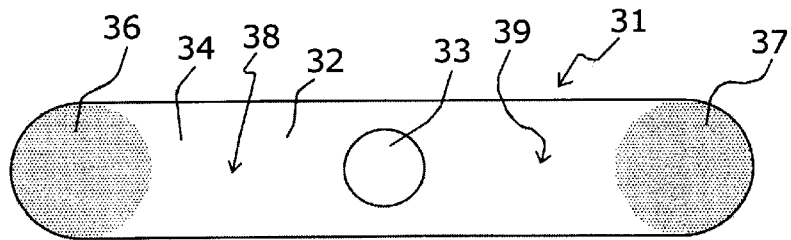
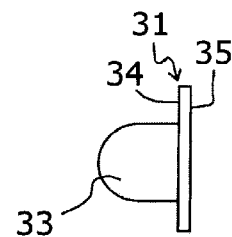
FIG. 1
PRIOR ART
FIG. 2
PRIOR ART
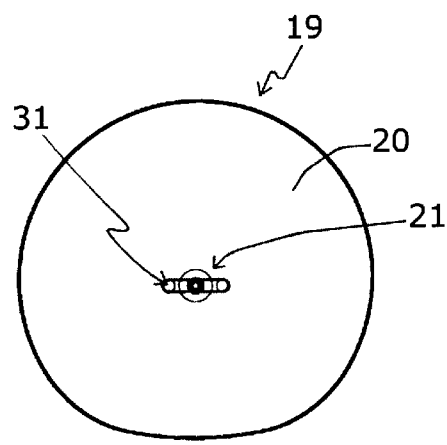
FIG. 3
PRIOR ART

PROSTHETIC IMPLANT VALVE COVER

BACKGROUND OF THE INVENTION

The present invention relates generally to prosthetic implants and particularly to an improved valve cover for such implants. Prosthetic implants, such as those used in reconstructive surgery or breast augmentation procedures, typically, have a valve that is used to fill the implant with a saline solution, gel or other material. A valve protective structure is provided to prevent access to the fill valve, however, the protective structure is removable for filling prior or during implementation by the surgeon. Subsequent filling, the valve entrance is again covered to protect the valve structure from bodily fluids and tissue ingrowth that may cause valve leakage.

Prior art implants typically use a protective valve structure which is generally comprised of a narrow strap with a plug located equidistant the strap ends. The plug is placed into the fill valve entrance to keep the entrance free of fluid and tissue. Each end of the prior art strap cover is adhered to the implant's exterior surface, thereby holding and protecting the plug inside the fill valve entrance.

Prior art strap cover configurations have been found to have various problems including holding the plug in place, and these strap configurations have also been found to permit tissue to grow in the area around the strap, particularly between the adhered ends of the strap and the plug. The tissue growth under and around the strap portions has been found to create problems to the implant recipient. First, the tissue growth may defeat the purpose of the strap by lifting the plug out of the fill valve entrance thereby creating space to enable fluid and tissue into the valve entrance. Second, subsequent implementation and during use, an implant has shown tendencies to move and rotate over time. Further, tissue has been found to grow between the strap and the implant's surface and being connected to the tissue surrounding the entire implant structure. It has been shown that the rotation of the implant may cause the tissue grown under and around the strap to twist which may result in a tumor in the form of a twisted chain of tissue that can be extremely painful for the implant recipient. (Dr. Miguel A. Mendez-Femandez, Plastic Reconstructive Surgery, September 1997, p. 750).

It is an object of the present invention to provide a protective valve cover for a prosthetic implant device which is easily applied to an implant, which is easily manipulated to provide access to the fill valve, which provides a more secure plug design to ensure proper protection of the fill valve, and which will keep the fill valve entrance free of fluid and tissue. It is also an object of this invention, to provide a valve cover structure that reduces the ability of tissue growth between the cover body and the implant surface so as to eliminate discomfort to the implant recipient as found with prior art valve straps.

Despite the need for a prosthesis valve cover which is adhered to the prosthetic implant body and which reduces the risk of pain to the recipient caused by prior art strap structures, none, as far as is known, have been proposed. The prosthetic implant valve cover of the present invention provides a structure which is constructed and arranged to be easily and effectively adhered to the implant body, which is adapted to permit the prosthetic implant to be easily filled and which solves the problems exhibited by prior art valve strap structures.

SUMMARY OF THE INVENTION

The present invention provides a valve cover adhered to the outside surface of an inflatable prosthetic implant and for covering the fill valve entrance. The prosthetic implant valve cover comprises a flexible body having an upper portion, a lower portion, and a fill valve entrance plug attached thereto. The upper portion has an outer periphery and is larger in area than the lower portion. The upper portion periphery has a bottom outer surface and which is constructed and arranged to be adhered continuously to the surface of the implant radially about the valve entrance.

The flexible valve cover body is preferably adhered through a curing process to the surface of the prosthetic implant, but may alternatively also be adhered by applying a medical grade silicone adhesive between the implant and valve cover surfaces. Preferably, the upper portion periphery has a textured bottom side to aid in adhesion of the valve cover body to the implant body during the curing process. The adhered portion is preferably continuous along the upper periphery and extends below an axis through the plug. The adhered implant valve cover creates a barrier extending around the upper portion and which keeps fluid and tissue from forming between the patch and the implant surface. The lower portion of the valve cover permits access to the fill valve of the implant.

The fill valve entrance plug is cylindrical in shape and is located generally at the center of the cover body and extends from the bottom of the cover body for placement into the fill valve of the implant. The plug is arranged to keep the fill valve entrance free of fluid and tissue between the valve cover body and the prosthetic implant surface.

These and other benefits of this invention will become clear from the following reference to the drawings.

BRIEF DESCRIPTION OF THE DRAWINGS

FIG. 1 is a bottom perspective view of a prior art valve strap;

FIG. 2 is a side elevational view of the prior art valve strap of FIG. 1;

FIG. 3 is a front plan view of a prosthetic implant having the prior art valve strap;

DESCRIPTION OF THE PREFERRED EMBODIMENT

Figure 4:
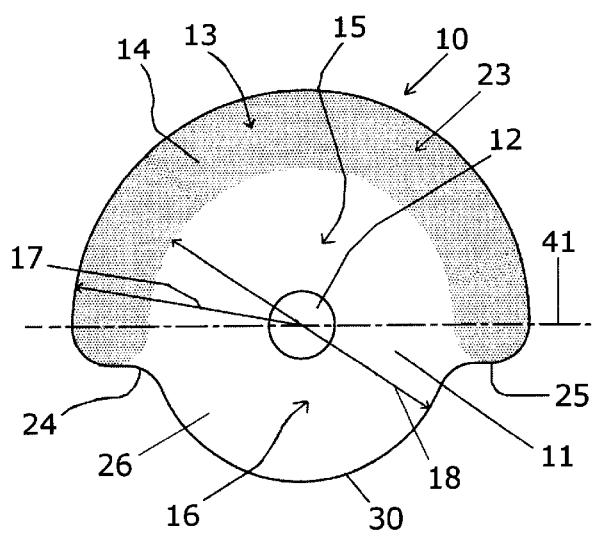
FIG. 4 is a bottom plan view of the prosthetic implant valve cover of the present invention.

The present invention relates to a prosthetic implant valve cover for sealing the fill valve of an inflatable prosthetic implant, such as an implant used in reconstructive surgery or breast augmentation. FIGS. 1–3 show a prior art valve cover or valve strap 31 adhered to a prosthetic implant 19. The prosthetic implant 19 has the valve strap 31 secured to the implant surface 20 and extending over the fill valve 21. The valve strap 31 extends across fill valve 21 and is adhered to the implant surface 20 at end areas 36 and 37. The valve patch 31 has an elongated body 32 having a valve plug 33 which is adapted to plug and seal the entrance of the fill valve 21. During implantation, the plug 33 of the valve cover is removed to expose the fill valve 21 for filling the implant with a predetermined material to a desired inflation level. The plug 33 is attached to the adhered strap body 32 and is reinserted after filling to protect the fill valve 21.

The valve strap body 32 is flexible and has a bottom surface 34 and a top surface 35. At opposite ends of the strap body 32 adhering areas 36 and 37 are disposed on the bottom surface 34. As a result, non-adhered portions 38 and 39 are formed between the valve plug 33 and the respective ends of the strap body. It is these non-adhered areas which have resulted in tissue growth problems and found to cause pain to the implant recipient when tissue has grown about these areas which inhibit the implant from flowing with surrounding tissue. These relatively fixed anchoring areas have resulted in discomfort to implant recipients.

Figure 5:
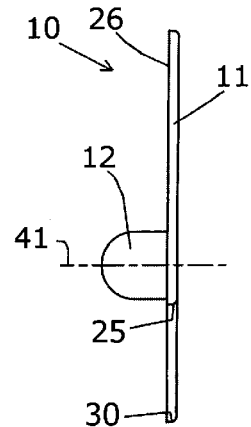
FIG. 5 is a side elevational view of the valve cover of FIG. 4.
Figure 8:
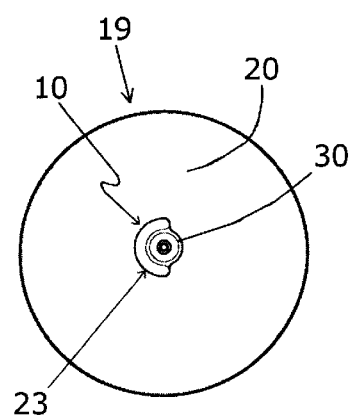
FIG. 8 is a front plan view of the valve cover applied to a prosthetic implant.

The present invention relates to a prosthetic implant valve cover 10, shown in FIGS. 4, 5 and 8. The valve cover 10 is shown attached to an inflatable prosthetic implant body 19 and is used to cover the fill valve 21 of a prosthetic implant 19. The valve cover 10 structure is comprised of a flexible cover body 11 and a fill valve entrance plug 12. The valve plug 12 is constructed and arranged to frictionally fit inside the filler valve entrance 22. The cover body 11 is constructed and arranged so that tissue growth about the implant is not problematic due to the valve cover structure and the implant surface 20.

The preferred embodiment comprises a valve cover body fabricated from silicone or like material and being similar to that of the prosthetic implant. As shown in FIGS. 4 and 5, the valve cover 10 has a generally circular disc shaped cover body 11 having an upper hemispherical portion 15 and a lower hemispherical portion 16. The generally hemispherical upper portion 15 has a peripheral area 13 which is shown to extend below the axis through the center of the plug 12 of the flexible valve cover body 11. The peripheral area 13, as will be further discussed, is shown to have a textured pattern 14 on the bottom side 26 of the valve cover body 11. For example, the lower hemispherical portion of the disc portion 16 having a radius of approximately 0.25 inches and the upper hemispherical portion of the disc portion 15 having a radius of approximately 0.375 inches. The transition areas 24 and 25 are shown between the two hemispheres 15 and 16 and the outer edges of the larger hemisphere radius 17 are rounded inwardly to create smooth transition areas 24 and 25.

As shown in FIG. 8, the valve cover body 11 is shown continuously adhered at least 180 degrees around the circumference of the plug 12, whereby the adhered portion 23 acts as a protective barrier reducing or eliminating any problems caused by tissue growth. The adhered area is shown to be continuous and to extend on each end below horizontal or center axis 41 which is shown to extend through plug 12 and generally defining the upper portion 15 and the lower portion 16. The cover body 11 has a radius 17, which permits it to be adhered to the implant surface 20 surrounding the fill valve 21. The radius 18 of the non-adhered portion 16 is smaller and covers the fill valve 21.

At the center of the portion 16 is a filler valve entrance plug 12, i.e. cylindrical in shape and having a radius of approximately 0.063 inches and extending from the cover body 11 a distance of approximately 0.125 inches. The end of the plug 12 is preferably rounded to engage the fill valve entrance. As shown in FIGS. 4 and 5 the bottom surface 26 of the outer portion 13 or the periphery of the upper hemisphere as depicted by radius 17 is textured to aid in adhering the valve body to the surface of the implant 20.

Figure 6:
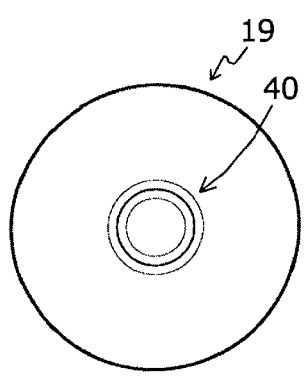
FIG. 6 is a rear view of a prosthetic implant.
Figure 7:
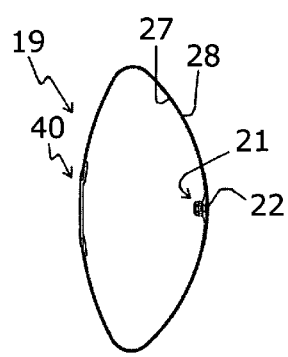
FIG. 7 is a side plan view of the prosthetic implant showing the fill valve and the valve cover.

As shown in FIGS. 6–8, the fill valve cover 10 is adhered at peripheral area 23 to the wall 20 of an inflatable prosthetic implant 19. The flexible body wall 20 with exterior surface 28 and interior surface 27 has a rear sealing patch 40 and a fill valve 21 including a valve entrance 22 at the front of the implant structure. The valve entrance 22 is accessible by lifting the bottom edge 30 of the lower portion 16 of the flexible valve cover body 11, as shown in FIG. 5.

Figure 9:
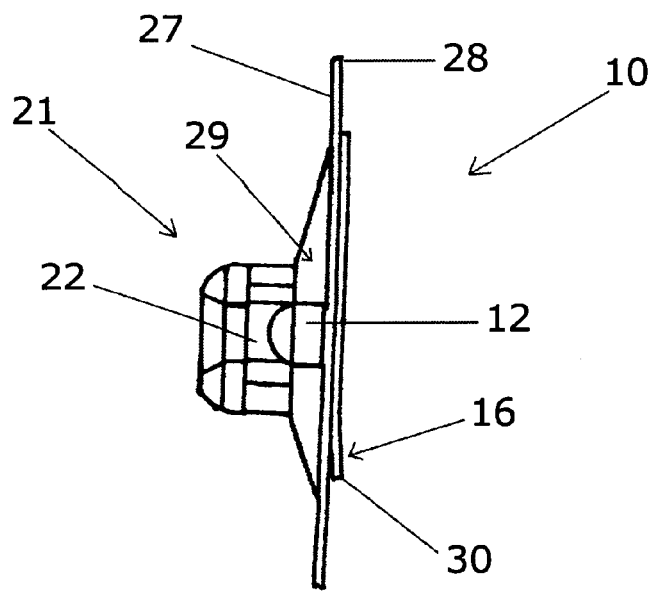
FIG. 9 is an enlarged view of the valve cover and showing the plug sealing the fill valve of t he prosthetic implant; a nd

As particularly shown in FIG. 9, prior to implantation, the surgeon obtains access to the opening 29 of the fill valve 21 by lifting the bottom 30 of the lower portion 16 of the valve cover 10. The plug 12 is removed from the valve opening 29 to expose the valve entrance 22. Subsequent filling, the plug 12 is reinserted into the valve opening 29.

Figure 10:
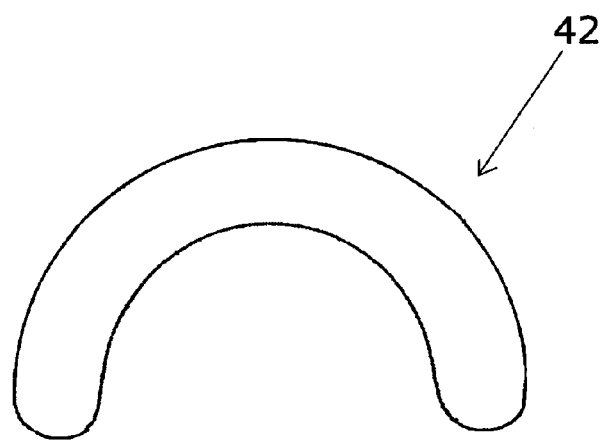
FIG. 10 is a top plan view of a strip of material used to adhere the valve cover to the implant surface.

Referring to FIGS. 4 and 5 the valve cover 10 is preferably adhered completely along the periphery area 13 of the upper hemisphere 15. For example, silicone adhesive may be utilized for this purpose. Preferably, the plug 12, the cover body 11, and implant 19 are constructed of a cured silicone composition and an adhesion strip 42 may be cut from sheeting material constructed of a similar but uncured silicone material. FIG. 10 is a top plan view of the adhesion strip 42, which conforms to the shape of the textured portion 14 of the valve cover 10. The adhesion strip 42, preferably, has a thickness of approximately 0.010 inches. The valve cover 10 is adhered to the implant surface by curing the silicone of the uncured strip 42 between the silicone surface 27 of the implant 20 and the silicone surface 13 of the bottom surface of the valve cover 26 prior to use. This process includes heating and applying pressure to the seal area for a predetermined time period. Preferably, a temperature of approximately 350° F. and a pressure of approximately 60 p.s.i. is applied to the area to be adhered for a duration of approximately four minutes. The adhesion process is aided by having the surface of the valve cover body textured as shown at 14. The textured bottom peripheral portion provides flow of the silicone material, when softened at 350° F., to yield a strong bond between the valve cover body and the implant body surface in the curing process.

From the foregoing description, it will be understood that various changes in the detailed construction of the invention may occur to persons skilled in the art without departing from the spirit and scope of the claimed invention. As many changes are possible to the embodiments of this invention, utilizing the teachings thereof, the description above, and the accompanying drawings should be interpreted in the illustrative, and not in the limited sense.

That which is claimed:

1. In a prosthetic implant having a body defining a cavity and having a fill valve structure having a valve entrance and a horizontal axis intersecting said valve entrance, a valve protective cover comprising:

a) a flexible body having an upper portion, a central portion, a lower portion and a bottom surface, said horizontal axis extending through said central portion of said flexible body and generally defining said upper portion and said lower portion, said lower portion having a lower lifting portion;

b) a valve plug extending from said bottom surface of said central portion of said valve protective cover body and being constructed and arranged to seal said valve entrance;

c) a continuous peripheral sealing area disposed on said bottom surface of said valve protective cover body, said sealing area extending through said upper portion and said horizontal axis and extending into said lower portion below said horizontal axis, and terminating above said lower lifting portion of said lower portion; and d) means of adhering said continuous peripheral sealing area of said bottom surface to said prosthetic implant body, whereby said valve cover seals said valve entrance and whereby said valve entrance is accessible by raising said lower lifting portion of said flexible body of said protective valve cover.

2. The valve cover of claim 1 wherein said upper portion of said flexible body has a rounded configuration having a first diameter and a lower portion having a second diameter and wherein said first diameter is larger than said second diameter.

3. The valve cover of claim 1 wherein said continuous peripheral area has a textured bottom surface prior to adhering said flexible body of said valve cover to said prosthetic implant body.

4. The valve cover of claim 1 wherein said valve cover body is constructed of the same material as said prosthetic implant body.

5. The valve cover of claim 4 wherein said material is silicone and wherein said adhering means comprises a heating and curing process.

6. The valve cover of claim 1 wherein said adhering means consists of a die-cut strip of uncured silicone sheeting that is cured between said implant body and said bottom surface of said valve cover body.

7. The valve cover of claim 6 wherein said uncured silicone sheeting has a thickness of approximately 0.010 inches.

8. The valve cover of claim 5 wherein said curing process consists of applying approximately 60 p.s.i. pressure and heat of approximately 350° F. to an area to be adhered for a duration of approximately four minutes.

9. The valve cover of claim 1 wherein said flexible body has a curved peripheral configuration with rounded transitional areas and wherein said rounded transitional areas extend between said upper and lower portions at said curved peripheral configuration of said flexible body.

10. The valve cover of claim 1 wherein said prosthetic implant is an implant for breast augmentation and is constructed of silicone.

11. A protective valve cover for adhering to the outside surface of an inflatable prosthetic implant having a fill valve with a fill valve entrance, comprising:

a) a flexible cover body having an upper portion, a lower portion, a center, and a bottom surface, said upper portion having a periphery whereby said valve cover is adhered at the bottom surface of said periphery to the surface of the implant; and b) a fill valve entrance plug extending from the bottom surface of said center of said flexible cover body and being constructed and arranged for placement into a fill valve entrance of an implant, whereby when said bottom surface of said upper portion periphery is adhered to an implant with said valve plug placed in the fill valve entrance, lifting of said lower portion of said flexible cover body provides access to the fill valve of the implant.

12. The valve cover of claim 11, wherein said bottom side of said upper portion periphery is textured prior to adhering to said implant body.

13. The valve cover of claim 11, wherein said upper portion has a first radius and said lower portion has a second radius and wherein said first radius is larger than said second radius.

14. A prosthetic implant in combination with a protective fill valve cover comprising:

a) an inflatable prosthetic implant having an outer surface and having a fill valve structure having a fill valve opening and a fill valve entrance;

b) a protective valve cover having a flexible body having an upper portion, a lower portion, a center, and a bottom surface, said upper portion having a peripheral area with a bottom surface is adhered to said outer surface of said implant, said lower portion extending across said fill valve structure;

c) a fill valve plug being constructed and arranged to be inserted into said fill valve opening, said fill valve plug extending from the bottom side of said flexible body for sealing placement into the fill valve entrance of said prosthetic implant; and d) said lower portion having a lifting portion at the bottom thereof to provide access to said fill valve plug.

15. The combination of claim 14, wherein said bottom side of said upper portion periphery is textured prior to adhering to said implant body.

16. The combination of claim 14, wherein said fill valve entrance plug is located at generally the center of said flexible body.

17. The combination of claim 14, wherein said upper portion has a first radius and said lower portion has a second radius and wherein said first radius is larger than said second radius.

18. The combination of claim 14, wherein said periphery of said valve cover body is cured to said exterior surface of said prosthetic implant.

19. The combination of claim 14, wherein said peripheral area is comprised of a textured surface.

20. The combination of claim 14, wherein said prosthetic implant body is constructed from a cured silicone material.

* * * * *